United States Patent [19]

Sawada et al.

[11] Patent Number: 4,664,658
[45] Date of Patent: May 12, 1987

[54] MEDICAL MATERIAL AND PROCESS FOR ITS PRODUCTION

[75] Inventors: Tsutomu Sawada; Kyoji Yoshida; Shozo Takano, all of Tsuchiura; Masanori Fujikawa, Komae, all of Japan

[73] Assignee: Mitsubishi Monsanto Chemical Company, Tokyo, Japan

[21] Appl. No.: 795,877

[22] Filed: Nov. 7, 1985

[30] Foreign Application Priority Data

Nov. 8, 1984 [JP] Japan .................................. 59-235872
Nov. 13, 1984 [JP] Japan .................................. 59-238819

[51] Int. Cl.$^4$ .................. A61M 5/325; A61M 25/005
[52] U.S. Cl. ........................................ 604/266; 428/36; 427/2; 128/334 R
[58] Field of Search ................ 428/36, 476.6, 497, 428/508-510, 520; 427/2, 301, 302; 604/255, 266, 403, 408, , 263, 266; 138/DIG. 22, 334 R; 625/1

[56] References Cited

U.S. PATENT DOCUMENTS

| | | |
|---|---|---|
| 3,886,947 | 6/1975 | Sawyer .......................... 128/334 R |
| 3,927,422 | 12/1975 | Sawyer .......................... 128/334 R |
| 3,955,012 | 5/1976 | Okamura et al. ...................... 427/2 |
| 4,060,081 | 11/1977 | Yanna et al. .......................... 623/1 |
| 4,167,045 | 9/1979 | Sawyer .................................. 623/1 |
| 4,178,271 | 12/1979 | Busch et al. .......................... 524/30 |
| 4,238,480 | 12/1980 | Sawyer .......................... 128/334 R |
| 4,321,117 | 3/1982 | Kaetsu et al. ........................ 424/19 |
| 4,326,532 | 4/1982 | Hammar ............................... 604/266 |
| 4,378,017 | 3/1983 | Kosugi et al. ............. 128/DIG. 22 |
| 4,378,435 | 3/1983 | Takagi et al. ........................... 427/2 |
| 4,411,754 | 10/1983 | Kaetsu ................................... 424/19 |
| 4,427,808 | 1/1984 | Stol et al. ............................... 524/24 |
| 4,478,961 | 10/1984 | Tanaka et al. ............. 128/DIG. 22 |
| 4,526,579 | 7/1985 | Aihpour ............................... 604/266 |
| 4,527,293 | 7/1985 | Eckstein et al. .................... 604/266 |
| 4,563,490 | 1/1986 | Stol et al. ............................... 524/24 |
| 4,582,762 | 4/1986 | Onohara et al. .................... 604/266 |

FOREIGN PATENT DOCUMENTS

| | | |
|---|---|---|
| 750770 | 5/1970 | Belgium ....................... 128/DIG. 22 |
| 0010621 | 5/1980 | European Pat. Off. ............ 604/265 |
| 0039983 | 3/1979 | Japan ........................... 128/DIG. 22 |
| 0904693 | 2/1982 | U.S.S.R. .................................... 623/1 |

Primary Examiner—C. Fred Rosenbaum
Assistant Examiner—Jerome R. Smith, Jr.
Attorney, Agent, or Firm—Oblon, Fisher, Spivak, McClelland & Maier

[57] ABSTRACT

A medical material comprising a shaped article made of a soft vinyl chloride resin composition, a layer formed on the shaped article and composed essentially of crosslinked gelatin having good bio-compatibility with a living body, and an intermediate bonding layer firmly bonding the crosslinked gelatin layer to the shaped article.

23 Claims, 3 Drawing Figures

MEDICAL MATERIAL AND PROCESS FOR ITS PRODUCTION

BACKGROUND OF THE INVENTION

Field of the Invention

The present invention relates to a medical material such as a blood transportation tube and a process for its production. More particularly, the present invention relates to such a medical material made of a soft vinyl chloride resin composition as the main constituent, which is made not to elute a substance toxic to blood, body fluid or medicinal liquid, such as a pyrogenous substance, and a process for its production.

Discussion of the Background

As a material for a transportation tube used for the collection from the human body, transportation or injection into a human body, of a blood or medicinal liquid in the medical fields such as blood collection, blood transfusion, fluid therapy or a blood circulation system for an artificial kidney, a composition composed essentially of a soft vinyl chloride resin has been used. The soft vinyl chloride resin has high levels of various properties required for the material of such transportation tubes, such as transparency, flexibility, resiliency, chemical resistance, high temperature properties and low temperature properties, and yet it is inexpensive. Therefore, it is suitable for use as a disposable article which is preferred also from the hygienic point of view.

However, when the soft vinyl chloride resin is used for such purposes, a plasticizer, stabilizer or other resin additives incorporated in the substrate resin are likely to elute to the blood or liquid during its use. Further, it has been pointed out that when brought in contact with blood, the soft vinyl chloride resin is likely to lead to hemolysis or blood coagulation.

In order to cope with the above-mentioned difficulties, it has been attempted to form a crosslinked gelatin layer on the inner surface of the tube made of the soft vinyl chloride resin, thereby to prevent the elution of the plasticizer, stabilizer or other resin additives to the blood or medicinal liquid and to solve the problems of hemolysis and blood coagulation at the same time.

SUMMARY OF THE INVENTION

Under these circumstances, it is an object of the present invention to provide a medical material such as a tube or sheet made of the soft vinyl chloride resin, which is made not to elute pyrogenous substances to blood or medicinal liquid and which is free from impurities.

Another object of the present invention is to provide a blood transportation tube, whereby the above-mentioned difficulties are substantially reduced.

According to the first aspect, the present invention provides a medical material comprising a shaped article made of a soft vinyl chloride resin composition, a layer formed on the shaped article and composed essentially of crosslinked gelatin having good bio-compatibility with a living body, and an intermediate bonding layer firmly bonding the crosslinked gelatin layer to the shaped article.

According to the second aspect, the present invention provides a process for producing such a medical material, which comprises uniformly wetting the surface of a shaped article made of a soft vinyl chloride resin composition, with a gelatin solution to form a non-crosslinked gelatin coating layer in a wet state, contacting a solution of a crosslinking agent to the coating layer to crosslink the non-crosslinked gelatin coating layer, removing any excessive solution of the crosslinking agent from the surface of the shaped article, and contacting the crosslinked gelatin layer of the shaped article to pyrogen-free water at a temperature of from 50° to 80° C. for at least two hours for cleaning.

According to the third aspect, the present invention provides a blood transportation tube comprising an outer tubular layer of a soft vinyl chloride resin composition, an inner tubular layer formed on the inside of the outer tubular layer and composed essentially of said crosslinked gelatin, and an intermediate bonding layer firmly bonding the inner tubular layer to the outer tubular layer.

According to the fourth aspect, the present invention provides a process for producing such a blood transportation tube, which comprises:

a first step of filling a tube made of a soft vinyl chloride resin composition, with a solution of a composition for forming a bonding layer, to uniformly wet the inner surface of the tube with the solution, then removing most of the solution from the tube, and drying the layer of the solution uniformly remaining on the inner surface of the tube to form a bonding layer;

a second step of filling the tube with a gelatin solution to uniformly wet the surface of the bonding layer with the gelatin solution, then removing most of the gelatin solution from the tube to form a non-crosslinked gelatin layer in a wet state on the surface of the bonding layer, thereafter filling the tube with a solution of a crosslinking agent for a non-crosslinked gelatin layer, to crosslink the non-crosslinked gelatin layer, and removing the solution of the crosslinking agent from the tube;

a third step of filling the tube with a plasticizing solution for the crosslinked gelatin layer, to have the plasticizing solution absorbed in the crosslinked gelatin layer in a wet state; and a fourth step of removing the plasticizing solution for the crosslinked gelatin layer from the tube and drying the inside of the tube.

BRIEF DESCRIPTION OF THE DRAWINGS

In the accompanying drawings.

DETAILED DESCRIPTION OF THE PREFERRED EMBODIMENTS

Figure 1:
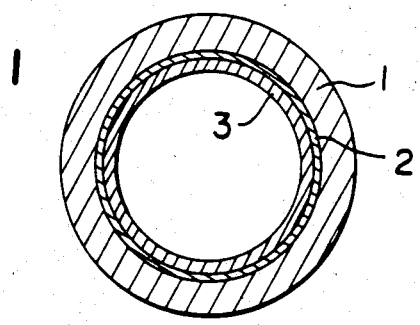
FIG. 1 is an enlarged cross-sectional view of a blood transportation tube according to the present invention.

Now, the present invention will be described in detail with reference to the preferred embodiments.

In the present invention, the vinyl chloride resin includes a polyvinyl chloride and a copolymer of vinyl chloride with other compounds copolymerizable therewith. As the compounds copolymerizable with vinyl chloride, there may be mentioned ethylene, propylene, vinyl acetate, acrylic acid, an alkyl ester of acrylic acid, methacrylic acid, an alkyl ester of methacrylic acid, maleic acid, fumaric acid, itaconic acid, acrylonitrile or vinylidene chloride.

To soften the above vinyl chloride resin, from 30 to 60 parts by weight of a plasticizer is incorporated relative to 100 parts by weight of the substrate resin. As such a plasticizer, there may be mentioned a phthalic acid derivative such as di-2-octyl phthalate, di-2-ethylhexyl phthalate or diisodecyl phthalate; an isophthalic acid derivative such as diisooctyl isophthalate; an adipic acid derivative such as dioctyl adipate; or other plasticizers such as tricresyl phosphate or epoxy-modified soybean oil.

In addition to the plasticizer, other resin additives such as a thermal stabilizer or a lubricant may also be incorporated into the above vinyl chloride resin, in an amount of not more than 5 parts by weight relative to 100 parts by weight of the substrate resin.

A usual blending and mixing technique, for instance, a method of using a ribbon blender, a Bumbury's mixer, a super mixer or other blending or mixing machine, may be employed for blending the plasticizer and resin additives to the substrate vinyl chloride resin.

The above-mentioned vinyl chloride resin is shaped into a tube or a sheet preferably by extrusion molding. The tube preferably has a cross-section of a circular shape with the outer diameter of not more than 10 mm, the inner diameter of at least 3 mm and a wall thickness of about 1 mm. The sheet preferably has a thickness of from 0.1 to 2 mm. In the following description, the invention will be described with respect to the tube as a representative of the shaped article.

Referring to the process for the production of a blood transportation tube, the first step comprises filling a tube made of a soft vinyl chloride resin composition, with a solution of a composition for forming a bonding layer to uniformly wet the inner surface of the tube with the solution, then discharging most of the solution from the tube, and drying the layer of the solution uniformly remaining on the inner surface of the tube to form a bonding layer. The bonding layer thus formed in the first step, has a function of firmly bonding the inner tubular layer composed mainly of crosslinked gelatin having good bio-compatibility with a living body, to the outer tubular layer.

As the effective ingredient in the solution of the composition for forming the bonding layer, there may be mentioned a hydrophilic water-insoluble material. Preferred is a polymer of a compound having a hydrophilic group, or a random copolymer or block copolymer of a compound having a hydrophilic group with another compound copolymerizable therewith. Particularly preferred is an acrylic resin.

An acrylic resin having the above properties is a polymer or copolymer of a monomer having a hydroxyl group. As the monomer having a hydroxyl group, there may be mentioned a hydroxyalkyl (meth)acrylate such as hydroxy methacrylate, hydroxymethyl methacrylate, 2-hydroxyethyl acrylate, 2-hydroxyethyl methacrylate, 2-hydroxyethylpropyl acrylate, 2-hydroxypropyl methacrylate, 3-hydroxypropyl acrylate, 3-hydroxypropyl methacrylate, 2-hydroxybutyl acrylate, 2-hydroxybutyl methacrylate, 4-hydroxybutyl acrylate, 4-hydroxybutyl methacrylate, 2-hydroxypentyl acrylate, 2-hydroxypentyl methacrylate, 6-hydroxyhexyl acrylate or 6-hydroxyhexyl methacrylate; or an acrylic monomer such as methacrylic acid, acrylamide, methacrylamide, diacetone acrylamide, diacetone methacrylamide, methylol acryloamide or methyl methacryloamide.

As the compounds copolymerizable with the above-mentioned hydroxyl group-containing monomer, there may be mentioned acrylic acid, methyl acrylate, methyl methacrylate, ethyl acrylate, ethyl methacrylate, propyl acrylate, propyl methacrylate, butyl acrylate, butyl methacrylate, pentyl acrylate, pentyl methacrylate, hexyl acrylate, hexyl methacrylate, heptyl acrylate, heptyl methacrylate, acrylonitrile, methacrylonitrile or vinyl acetate.

The solution of the composition for forming a bonding layer is a solution of the above polymer in a liquid medium (solution type) or a dispersion of the polymer in a liquid medium (emulsion type). As the liquid medium, there may be employed water, toluene, benzene, ethyl acetate, ethyl alcohol, isopropyl alcohol, n-hexyl alcohol, cyclohexanol or a mixture thereof. In the case of the emulsion type, it is preferred to stabilize the system by incorporating an emulsifier.

In the first step, the tube to constitute the outer tubular layer, is filled with the solution of the composition for forming a bonding layer, to uniformly wet the inner surface of the tube with this solution. Then, most of the solution is discharged from the tube to permit the solution to remain on the inner surface of the tube in a uniform thickness. As the liquid medium of the remaining solution is evaporated by drying, a thin bonding layer is formed. If the bonding layer is too thin, it is difficult to control the thickness uniformly over the entire surface, and such a thin layer will not properly function as a bonding layer. On the other hand, if the bonding layer is too thick, the flexibility of the bonding layer will be impaired, and the final product is likely to be defective as the finally obtainable tube is susceptible to breakage when bent. The thickness of the bonding layer is preferably from 2 to 10 $\mu$m, more preferably from 3 to 6 $\mu$m.

The thickness of the bonding layer may be controlled by properly adjusting the concentration of the solution of the composition for forming the bonding layer. The concentration of the solution is preferably from 0.01 to 2% by weight of the solid content. To dry the layer of the solution uniformly remaining on the inner surface of the tube, it is preferred to place the tube in a heating furnace (oven) adjusted to a temperature of from 60° to 140° C., and supply dried air from one end of the tube. The temperature of the heating furnace may properly be adjusted depending upon the boiling point of the liquid medium of the solution. However, if the temperature is lower than 60° C., it takes long time for drying and bacteria are likely to propagate, such being undesirable. On the other hand, if the temperature is higher than 140° C., the outer tubular layer made of a soft vinyl chloride resin is likely to be softened, colored or thermally decomposed, such being undesirable. The air to be supplied to the tube is pressurized. If the pressure is too small, the evaporated portion of the liquid medium can not be transported. On the other hand, if the pressure is too high, the bonding layer is likely to be partially transported to form a waved surface, such being undesirable. Therefore, the pressure of the air to be supplied to the tube is preferably selected within a range of from 0.01 to 2 kg/cm$^2$.

In the second step, the tube thus processed by the first step is filled with a gelatin solution to uniformly wet the surface of the bonding layer with the gelatin solution. Then, most of the gelatin solution is removed from the tube to form a non-crosslinked gelatin coating layer in a wet state on the surface of the bonding layer. Then, this tube is filled with a solution of a crosslinking agent for crosslinking the non-crosslinked gelatin coating layer, to crosslink the non-crosslinked gelatin layer.

The crosslinked gelatin layer has good biocompatibility with a living body, and has a function to prevent the elution of the plasticizer, stabilizer or other resin additives incorporated in the outer tubular layer, to blood.

Gelatin is obtained by the hydrolysis of collagen to polypeptide chains, or by the further splitting of such isolated polypeptide chains, and has a molecular weight of from 15,000 to 250,000.

As a solvent for gelatin, there may be mentioned water, methyl alcohol, ethyl alcohol, n-propyl alcohol, isopropyl alcohol, secondary propyl alcohol, tertiary propyl alcohol, glycerol, propylene glycol or acetone. These solvents may be used alone or in combination as a mixture of two or more different kinds.

For filling the tube with the gelatin solution, the gelatin solution is kept at a temperature high enough to avoid the solidification of gelatin, preferably at a temperature of at least 30° C., more specifically from 35° to 60° C. After uniformly wetting the surface of the bonding layer formed in the first step, with this gelatin solution, most of the gelatin solution is removed from the tube. Then, the temperature of tube is lowered to a level of not higher than 30° C., preferably not higher than 10° C., to solidify the gelatin in the gelatin solution formed on the surface of the bonding layer and to form a non-crosslinked gelatin coating layer in a wet state. The thickness of the non-crosslinked gelatin coating layer may be adjusted by the concentration of the gelatin solution or by the temperature of the gelatin solution filled in the tube. Namely, the higher the concentration or the lower the temperature, the thicker the gelatin layer formed on the inner surface of the tube.

If the concentration of the gelatin solution is too high, the viscosity tends to be too high even when the temperature of the gelatin solution is raised, whereby it becomes difficult to obtain a non-crosslinked gelatin coating layer in a wet state in a uniform thickness on the bonding layer, or the gelatin coating layer tends to be too thick. If the gelatin coating layer is too thick, the non-crosslinked gelatin coating layer is susceptible to breakage when the tube is filled with the solution of a crosslinking agent, and it is difficult to obtain a blood transportation tube of good quality. On the other hand, if the concentration of the gelatin solution is too low, the non-crosslinked gelatin coating layer tends to be too thin, whereby it becomes difficult to adequately control the elution of the plasticizer, stabilizer or other resin additives from the outer tubular layer made of a soft vinyl chloride resin composition, to blood. Therefore, the concentration of the gelatin solution is preferably such that the gelatin content is from 5 to 20% by weight, more preferably from 8 to 15% by weight.

The tube formed with such a non-crosslinked gelatin layer in a wet state, is then filled with a solution of a crosslinking agent for the non-crosslinked gelatin layer, to crosslink the gelatin layer. By the crosslinking of the gelatin layer, the elution of the plasticizer, stabilizer or other resin additives from the outer tubular layer to blood is remarkably decreased.

The solution of the crosslinking agent for the gelatin layer is an aqueous solution of a crosslinking agent. As such a crosslinking agent, there may suitably be used an aldehyde, an isocyanate, an acid chloride, a sulfonyl chloride, a chloroformate, an epoxy or epichlorohydrin. Among them, an aldehyde such as formaldehyde, glutaric aldehyde or glyoxal, is particularly preferred.

The concentration of the solution of the crosslinking agent is preferably from 0.1 to 2% by weight of the crosslinking agent.

In order to crosslink the non-crosslinked gelatin layer in a wet state, the tube is filled with the solution of the crosslinking agent and is kept in the filled state at room temperature for from 30 minutes to a few hours. The crosslinking reaction takes place during this period, whereby the gelatin layer is modified. Thereafter, the solution of the crosslinking agent is removed from the tube. For the purpose of removing any excessive crosslinking agent still remaining on the surface of the tube, it is preferred to pass pyrogen-free water through the tube.

In a preferred embodiment of the invention, the tube is, after the removal of the solution of the crosslinking agent, filled with pyrogen-free water heated to a temperature of from 50° to 80° C. to clean the crosslinked gelatin layer. This cleaning is intended to wash off non-crosslinked gelatin in the crosslinked gelatin layer, an unreacted crosslinking agent and undesirable substances contained in the gelatin. In order to wash off these substances, it is possible to either continuously supply warm water to the tube after the completion of the above-mentioned step, or fill the tube with warm water and leave it to stand still for a predetermined period of time under warm condition, and then discharge the water. From the economical point of view, the latter is preferred.

If the temperature of the cleaning water is less than 50° C., bacteria are likely to propagate. On the other hand, if the temperature is higher than 80° C., the tube is likely to undergo property changes or the crosslinked gelatin layer is likely to peel off, such being undesirable. When the tube is filled with pyrogen-free water heated to a level of from 50° to 80° C. and left to stand under warm condition, it is preferred to leave the filled tube to stand still for at least 2 hours. After completion of leaving it to stand still, the warm water is discharged from the tube, and it is preferred to wash the crosslinked gelatin layer with fresh pyrogen-free water.

After completion of the cleaning of the crosslinked gelatin layer, the tube can be used as it is, for liquid therapy. However, the crosslinked gelatin layer lacks in flexiblity. Therefore, it is preferred to conduct after-treatment to have a plasticizing substance absorbed so that the gelatin layer is plasticized.

Namely, in the third step, while the crosslinked gelatin layer on the inner surface of the tube after the removal of the solution of the crosslinking agent, is still in a wet state, the tube is filled with a plasticizing solution for the crosslinked gelatin layer to have the plasticizing solution absorbed in the crosslinked gelatin layer.

The crosslinked gelatin layer is extremely brittle when dried, and as such, can not follow the flexural properties of the outer layer made of a soft vinyl chloride resin, and is likely to break even with a small deformation. Such britfleness of the crosslinked gelatin layer is substantially reduced when the plasticizing solution is absorbed in the crosslinked gelatin layer.

As the plasticizing solution for the crosslinked gelatin layer, an aqueous solution of glycerin is preferred. This plasticizing solution is preferably an aqueous solution containing from 5 to 50% by weight, more preferably from 20 to 40% by weight, of glycerin.

In order to plasticize the crosslinked gelatin layer, the tube is filled with the plasticizing solution and is kept in the filled state at room temperature for from 1 to 30 minutes.

In the fourth step, the plasticizing solution is removed from the tube after the completion of the third step, and the inside of the tube is dried. The drying of the inner surface of the tube in this step may be conducted under the same conditions as those for drying the liquid medium of the solution of the composition in the first step.

In the process of the present invention, water used is required to be pyrogen-free water, and the gelatin, crosslinking agent, glycerin, etc. used are required to be selected so that they do not contain substances toxic to the human body.

When the medical material of the present invention is a tube, it is useful as a liquid transportation tube for the collection from the human body, the transportation, or the injection into the human body, of blood or medicinal liquid in the medical fields such as blood collection, blood transfusion, fluid therapy or a blood circulation system of an artificial kidney. When the shaped article is a sheet, it is used for the preparation of a bag-like container.

The present invention provides the following remarkable effects, and its industrial value is extremely high.

(1) The medical material such as a blood transportation tube according to the present invention has a coating layer composed essentially of crosslinked gelatin having excellent bio-compatibility with a living body, and thus is highly wettable with blood or medicinal liquid, whereby adhesion of bubbles on the surface of the shaped article or a trouble of the flow rate change can be avoided.

(2) The medical material such as a blood transportation tube according to the present invention has a coating layer composed essentially of crosslinked gelatin, whereby blood or medicinal liquid is not brought in direct contact with the tube or sheet made of a soft vinyl chloride resin, and the elution of the plasticizer, stabilizer or other resin additives incorporated to the soft vinyl chloride resin, to the blood or medicinal liquid, can be substantially decreased.

(3) When the crosslinked gelatin layer formed on the surface of the tube or sheet is washed with pyrogen-free warm water according to the present invention, it is possible to obtain a medical material wherein the crosslinked gelatin layer contains no substantial pyrogenous substances or other undesirable substances.

Now, the present invention will be described with reference to Examples. However, it should be understood that the present invention is by no means restricted to these specific Examples.

EXAMPLE 1

First Step

A commercially available soft polyvinyl chloride tube for artificial dialysis having an outer diameter of 7 mm, an inner diameter of 5 mm and a length of 6 m, was used.

10 parts by weight of a one polymer type acrylic resin adhesive (Oribain BPS-3233, manufactured by Toyo Ink K.K., solvent: ethyl acetate, solid content: 36.5% by weight) was diluted with 90 parts by weight of ethyl acetate. To 10 parts by weight of this diluted liquid, 90 parts by weight of ethyl alcohol was added to obtain a solution of a composition for forming a bonding layer having an adhesive concentration of 1% by weight.

The solution of the above composition was filled in the above-mentioned tube to uniformly wet the inner surface of the tube with the solution, and then most of the solution was removed from the tube. The tube with a coating layer of the composition uniformly remained on the inner surface of the tube, is placed in a heating furnace adjusted to the temperature of 80° C., and a compressed air of 0.4 kg/cm$^2$ was supplied from one end of the tube, and this operation was continued for 10 minutes.

On the inner surface of the tube thereby obtained, there was formed a bonding layer having a thickness of about 4 $\mu$m.

The presence or absence of the remaining solvent, ethyl acetate, in the bonding layer was inspected by gas chromatography, whereby no ethyl acetate was detected.

Second Step 12 parts by weight of gelatin (JIS special grade, manufactured by Kabushiki Kaisha Nippi), 60 parts by weight of pyrogen-free water and 28 parts by weight of ethyl alcohol were mixed, and the mixture was heated to 60° C. to obtain a gelatin solution.

The gelatin solution maintained at 60° C. was filled in the tube after completion of the first step, to uniformly wet the surface of the bonding layer of the tube with the gelatin solution, and then most of the gelatin solution was removed from the tube. Then, the tube was placed in a cooling chamber adjusted to a temperature of 5° C. to harden the gelatin, whereby a non-crosslinked gelatin layer having a thickness of about 300 $\mu$m in a wet state was formed on the surface of the bonding layer.

This tube was filled with an aqueous solution containing 0.5% by weight of glutaraldehyde, and left to stand in a warm chamber adjusted to a temperature of 50° C. for 30 minutes for a crosslinking reaction to crosslink the non-crosslinked gelatin layer.

The solution of the crosslinking agent was discharged from the tube, and then pyrogen-free water was continuously passed through the tube at a flow rate of 100 cc/min for 10 minutes to wash out excessive aldehyde.

Third Step

While the crosslinked gelatin layer after completion of the second step was still in a wet state, an aqueous solution containing 20% by weight of glycerin was filled in the tube, and the tube was left to stand under such a condition at room temperature for 10 minutes to have the glycerin absorbed in the crosslinked gelatin layer. Then, the aqueous glycerin solution was discharged from the tube.

Fourth Step

The tube after completion of the third step was placed in a heating furnace adjusted to a temperature of 80° C. Compressed air of 0.4 kg/cm$^2$ was supplied from one end of the tube, and this operation was continued for 10 minutes to dry the inside of the tube.

The tube thereby obtained had a crosslinked gelatin layer having a thickness of about 30 $\mu$m, and had a cross-sectional structure as shown by the enlarged cross-sectional view in FIG. 1. In FIG. 1, reference numeral 1 indicates the outer layer of the tube made of polyvinyl chloride, numeral 2 indicates the bonding layer, and numeral 3 indicates the inner layer made of crosslinked gelatin.

The crosslinked gelatin layer was peeled off from the tube, and the concentration of glycerin contained in the layer was measured and found to be about 30% by weight.

Inspection of the Elution of the Plasticizer from the Tube

Figure 2:
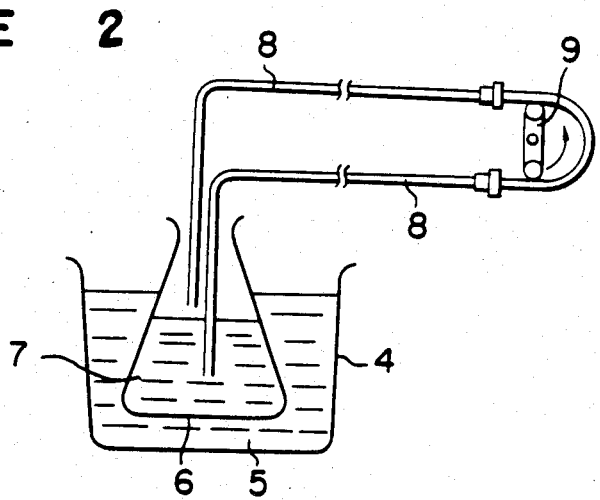
FIG. 2 is a diagrammatic view of an apparatus used for a test for the elution of a plasticizer from the tube.

The tube obtained in Example 1 was set up as shown diagrammatically in FIG. 2, and a horse blood serum was circulated, whereby the amount of the elution of the plasticizer dioctyl phthalate was analyzed. In FIG. 2, reference numeral 4 is a container for warm water, numeral 5 is warm water maintained at a temperature of 40° C., numeral 6 is a container for a horse blood serum 7, numeral 8 is the tube, and numeral 9 is a rotary pump. The horse blood serum was continuously circulated for 10 hours through the tube having a length of 6 m, and then the amount of elution of dioctyl phthalate was analyzed by gas chromatography, and found to be 0.5 ppm.

COMPARATIVE EXAMPLE 1

By using the same type of a soft polyvinyl chloride tube as used in Example 1, a horse blood serum was circulated in the same manner as above, whereby the amount of elution of dioctyl phthalate was analyzed and found to be 5.5 ppm.

EXAMPLE 2

A tube for fluid therapy was prepared in the same manner as in Example 1 except that after the crosslinking of the gelatin layer, the tube was filled with pyrogen-free water heated to a temperature of 70° C. and left to stand in that state in an atmosphere adjusted to a temperature of 70° C. for 10 hours, and then the water was discharged from the tube, and the inside of the tube was washed with fresh pyrogen-free water by continuously passing the pyrogen-free water through the tube at a flow rate of 100 cc/min for 10 minutes.

The tube for fluid therapy thereby obtained had a crosslinked gelatin layer having a thickness of about 30 μm, and had a cross-sectional structure as shown by the enlarged cross-sectional view in FIG. 1.

The crosslinked gelatin layer was peeled off from the tube, and the concentration of glycerin contained in the layer was measured and found to be about 30% by weight.

Evaluation Test for the Tube

The tube obtained in Example 2 was set up as shown diagrammatically in FIG. 2, and a physiological sodium chloride solution was circulated for 5 hours through the tube having a length of 6 m. The solution after the circulation was analyzed with respect to the following items. The results are shown in Table 1.

In this Example, referring to FIG. 2, reference numeral 4 is a container for warm water, numeral 5 is warm water at a temperature of 40° C., numeral 6 is a container, numeral 7 is the physiological sodium chloride solution, numeral 8 is the tube, and numeral 9 is a rotary pump.

(a) Ultraviolet Absorption Spectrum

In accordance with the testing method for the approval of a dialysis type artificial kidney, the absorbance of ultraviolet rays having a wave length of from 220 to 350 nm was measured with respect to the test solution with a thickness of 10 mm, as compared with a blank test solution. If the absorbance is not higher than 0.1, the tube is satisfactory.

(b) Pyrogenous Substance

In accordance with a testing method for pyrogenous substance by the Pharmacopeia of Japan, a test solution was tested as compared with a blank test solution, whereby a Limrous method (wherein a horseshoe-crab blood serum was employed) was used. The test results are evaluated by the following standards.

(−): No pyrogenous substance was detected.
(+): Pyrogenous substance was detected.

(c): The amount of remaining glutaraldehyde

In accordance with a colorimetric test by means of a Nessler reagent

EXAMPLES 3 to 6 and COMPARATIVE EXAMPLES 2 to 4

Tubes were prepared in the same manner as in Example 2 except that the conditions for the washing of the inside of the tube with water were changed as identified in Table 1.

With respect to the tubes thus obtained, evaluation tests were conducted in the same manner as in Example 2. The results are shown in Table 1.

EXAMPLE 7

Preliminary Step

To 100 parts by weight of polyvinyl chloride ($\bar{P}$=1400), 45 parts by weight of dioctyl phthalate was blended, and the mixture was extrusion-molded to obtain a sheet having a size of 50×50 cm and a thickness of 0.2 mm.

On one side of this sheet, the same type of a one polymer type acrylic resin adhesive as used in Example 2 was coated by a gravure printing method. This sheet was placed in a heating furnace adjusted to a temperature of 80° C., and dried.

Step for Forming a Crosslinked Gelatin Layer

On the undercoating layer of the sheet thus formed, the same type of a gelatin solution as used in Example 2 was coated by a knife coating method to form a non-crosslinked gelatin layer having a thickness of about 300 μm in a wet state.

This sheet was dipped in the same type of an aqueous glutaraldehyde solution as used in Example 2 and left to stand for 30 minutes to crosslink the non-crosslinked gelatin layer.

Washing of the Sheet

The crosslinked gelatin layer of the sheet thereby obtained was washed with pyrogen-free water to roughly remove the excess solution of the crosslinking agent, and then the sheet was dipped in pyrogen-free water maintained at a temperature of 70° C. for 10 hours.

Then, the sheet was taken out of the dipping solution, and washed with fresh pyrogen-free water.

Step for Aftertreatment

While the crosslinked gelatin layer after the washing of the sheet was still in a wet state, this sheet was dipped in a 20% glycerin aqueous solution to have the glycerin absorbed in the crosslinked gelatin layer.

The sheet taken out from the aqueous glycerin solution, was placed in an oven heated to a temperature of 80° C. and left to stand for 30 minutes to dry the surface of the sheet.

Figure 3:
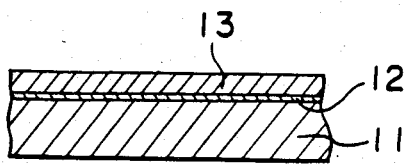
FIG. 3 is an enlarged sectional view of the sheet obtained in Example 7.

The sheet thereby obtained had a crosslinked gelatin layer having a thickness of about 30 μm, and had a cross-sectional structure as shown by the enlarged cross-sectional view in FIG. 3.

In FIG. 3, reference numeral 11 is a polyvinyl chloride sheet, numeral 12 is the undercoating layer, and numeral 13 is the crosslinked gelatin layer.

Evaluation Tests of the Sheet

The sheet obtained in Example 7 was cut into a size so that the total surface area of the front and rear sides was 1200 cm$^2$, this sheet was further cut into a size of 5 cm in length and 0.5 cm in width, then washed with pyrogen-free water and dried in room temperature. The sample sheet thereby obtained was placed in a glass container having a capacity of 300 ml, and 200 ml of a physiological sodium chloride solution was accurately added. After closing the container with a stopper, the container was heated at 121° C. for 1 hour by means of an autoclave sterilizer, and then left to cool to room temperature. The solution thereby obtained was used as a test solution.

With respect to this test solution, the tests (a), (b) and (c) as disclosed in Example 2 were conducted. The results are shown in Table 1.

TABLE 1

| Examples | Temperature of washing water (°C.) | Immersed time (hrs) | Ultra-violet spectrum | Pyrogenous substance | Remaining glutaraldehyde (ppm) |
|---|---|---|---|---|---|
| Example 2 | 70 | 10 | 0.03 | (−) | 0.1 or less |
| Example 3 | 50 | 10 | 0.08 | (−) | 0.4 |
| Example 4 | 80 | 10 | 0.03 | (−) | 0.1 or less |
| Example 5 | 70 | 2 | 0.08 | (−) | 1.0 |
| Example 6 | 70 | 20 | 0.03 | (−) | 0.1 or less |
| Example 7 | 70 | 10 | 0.03 | (−) | 0.1 or less |
| Comparative Example 2 | 40 | 10 | 0.13 | (+) | 0.5 |
| Comparative Example 3 | 90 | 10*[1] | 0.03 | (−) | 0.1 or less |
| Comparative Example 4 | 70 | 1 | 0.25 | (+) | 20 |

Note:
*[1] Peeling of the crosslinked gelatin layer from the tube was observed.

From Table 1, the following is evident.

(1) When the temperature of the washing water is from 50° to 80° C. and the time for contact of the crosslinked gelatin layer with the washing water is at least 2 hours, the pyrogenous substance contained in the crosslinked gelatin layer and the amount of the remaining aldehyde, can be reduced to a satisfactory level (Examples 2 to 7).

(2) Whereas, when the temperature of washing water is too low (Comparative Example 2) or the time for contact of the gelatin layer with the washing water is too short (Comparative Example 4), the washing of the crosslinked gelatin layer tends to be inadequate, and it is likely that the pyrogenous substance is detected or unreacted aldehyde at an undesirable level is detected. Further, if the temperature of washing water is too high, it is likely that peeling of the crosslinked gelatin layer takes place.

We claim:

1. A medical article, comprising a shaped article made of a soft vinyl chloride resin composition, a layer formed on the shaped article and composed essentially of crosslinked gelatin having a good bio-compatibility with a living body, and an intermediate bonding layer firmly bonding the crosslinked gelatin layer to the shaped article.

2. The medical article of claim 1, wherein the said shaped article is a tube.

3. The medical article of claim 1, wherein the said shaped article is a sheet.

4. A blood transportation tube comprising an outer tubular layer made of a soft vinyl chloride resin composition, an inner tubular layer formed on the inside of the said outer tubular layer and being composed essentially of crosslinked gelatin having a good bio-compatibility with a living body, and an intermediate bonding layer firmly bonding the said inner tubular layer to the said outer tubular layer.

5. The medical article of claim 1, wherein the said vinyl chloride resin composition is polyvinyl chloride or a copolymer of vinyl chloride with ethylene, propylene, vinyl acetate, acrylic acid, and alkyl ester of acrylic acid, methacrylic acid, and alkyl ester of methacrylic acid, maleic acid, fumaric acid, itaconic acid, acrylonitrile or vinylidene chloride.

6. The blood transporation tube of claim 4, wherein the said soft vinyl chloride resin composition is polyvinyl chloride or a copolymer of vinyl chloride with ehylene, propylene, vinyl acetate, acrylic acid, an alkyl ester of acrylic acid, methacrylic acid, and alkyl ester of methacrylic acid, maleic acid, fumaric acid, itaconic acid, acrylonitrile or vinylidene chloride.

7. The medical article of claim 1, wherein the said vinyl chloride resin contains from 30 to 60 parts by weight of plasticizer per 100 parts by weight of the substrate resin.

8. The blood transporation tube of claim 4, wherein the said vinyl chloride resin comprises 30 to 60 parts by weight of a plasticizer per 100 parts by weight of the substrate resin.

9. The medical article of claim 7, wherein the said plasticizer comprises a phthalic acid derivative including di-2-octyl phthalate, di-2-ethyhexyl phthalate or diisodecyl phthalate; and isophthalic acid derivative including diisooctyl isophthalate; and adipic acid derivative including dioctyl adipate; triceresyl phosphate; or an epoxy-modified soybean oil.

10. The blood transporation tube of claim 8, wherein the said plasticizer comprises a phthalic acid derivative including di-2-octyl phthalate, di-2-ethylhexyl phthalate or diisodecyl phthalate; an isophthalic acid derivative including diisooctyl isophthalate; and adipic acid derivative including dioctyl adipate; tricresyl phosphate; or an epoxy-modified soybean oil.

11. The medical article of claim 1, wherein the said resin comprises a thermal stabilizer or a lubricant.

12. The blood transporation tube of claim 4, wherein the said resin comprises a thermal stabilizer or a lubricant.

13. The medical article of claim 2, wherein the said tube has an outer diameter of no more than 10 mm and an inner diameter of at least 3 mm.

14. The medical article of claim 13, wherein the said sheet has a thickness of from 0.1 to 2 mm.

15. The blood transportation tube of claim 4, wherein the said tube has an outer diameter of not more than 10 mm and an inner diameter of at least 3 mm.

16. The medical article of claim 1, wherein the said intermediate bonding layer comprises a hydrophilic water-insoluble material.

17. The blood transportation tube of claim 4, wherein the said intermediate bonding layer comprises a hydrophilic water-insoluble material.

18. The medical article of claim 1, wherein the said intermediate bonding layer is a polymer of a compound having an hydrophilic group, or a random copolymer of block copolymer of a compound having a hydrophilic group with another compound copolymerizable therewith.

19. The blood transportation tube of claim 4, wherein the said intermediate bonding layer is a polymer of a compound having a hydrophilic group, or a random copolymer or block copolymer of a compound having a hydrophilic group with another compound copolymerizable therewith.

20. The medical article of claim 1, wherein the said intermediate bonding layer comprises an acrylic resin.

21. The blood transportation tube of claim 15, wherein the said intermediate bonding layer comprises an acrylic resin.

22. The medical article of claim 1, wherein the said gelatin is obtained by the hydrolysis of collagen to polypeptide chains, or by the further splitting of such isolated polypeptide chains, and wherein the said gelatin has a molecular weight of from 15,000 to 250,000.

23. The blood transportation tube of claim 4, wherein the said gelatin is obtained by the hydrolysis of collagen to polypeptide chains, or by the further splitting of such isolated polypeptide chains, and wherein the said gelatin has a molecular weight of from 15,000 to 250,000.

* * * * *